United States Patent [19]

Van Duin

[11] Patent Number: 4,778,570
[45] Date of Patent: Oct. 18, 1988

[54] PROCESS FOR DETERMINING THE ORGANIC HALOGEN CONTENT OF ORGANIC SAMPLES

[75] Inventor: Pieter J. Van Duin, Ee Noordwijk, Netherlands

[73] Assignee: Nederlandse Centrale Organisatie Voor Toegepast-Natuurwetenschappelijk Onderzoek, Netherlands

[21] Appl. No.: 706,852

[22] PCT Filed: Jun. 8, 1984

[86] PCT No.: PCT/NL84/00017
§ 371 Date: Feb. 6, 1985
§ 102(e) Date: Feb. 6, 1985

[87] PCT Pub. No.: WO84/04968
PCT Pub. Date: Dec. 20, 1984

[30] Foreign Application Priority Data

Jun. 10, 1983 [NL] Netherlands ................. 8302076

[51] Int. Cl.$^4$ ............................. G01N 27/44
[52] U.S. Cl. ...................... 204/1 T; 204/405; 436/124; 436/126; 436/177
[58] Field of Search .............. 204/1 B, 405, 128; 436/124, 125, 126, 150, 175, 177, 178

[56] References Cited

U.S. PATENT DOCUMENTS

| | | |
|---|---|---|
| 3,413,199 | 11/1968 | Morrow, Jr. ............... 204/1 B |
| 3,876,514 | 4/1975 | Baizer ................. 204/72 |
| 4,028,201 | 6/1977 | Tyssee ............... 204/73 R |
| 4,072,584 | 2/1978 | Cipris et al. ............. 204/291 |
| 4,160,802 | 7/1979 | White et al. ............ 436/160 |
| 4,539,083 | 9/1985 | Samejima et al. ......... 204/128 |

FOREIGN PATENT DOCUMENTS

| | | |
|---|---|---|
| 1086918 | 8/1960 | Fed. Rep. of Germany . |
| 2079881 | 11/1971 | France . |
| 2239920 | 2/1975 | France . |
| 576536 | 1/1975 | U.S.S.R. .................. 204/1 B |
| 711812 | 7/1954 | United Kingdom . |
| 1098653 | 1/1968 | United Kingdom . |

OTHER PUBLICATIONS

Farwell et al., *Anal. Chem.*, vol. 47, No. 6, Amer. Chem. Soc. (Washington, D.C.), 1975, pp. 895–903.
Peeters et al., *J. Org. Chem.*, vol. 40, No. 3, Amer. Chem. Soc., (Wash., D.C.), 1975, pp. 312–318.
Tingane, *Electroanalytical Chemistry*, 2nd Ed., Interscience Publishers, Inc., (New York), 1958, pp. 373–380.
Indirect Polarographic Microdetermination of Fluorine in Fluro-Organic Compounds After Oxygen-Flask Combustion, Y. A. Gawargious, A. Besada, B. N. Faltaoos, Analytical Chemistry, vol. 47, No. 3, pp. 502–505, Mar. 1975, American Chemical Society, Books and Journals Division, Washington, D.C. 20036.

*Primary Examiner*—Barry S. Richman
*Assistant Examiner*—Robert J. Hill, Jr.
*Attorney, Agent, or Firm*—Webb, Burden, Ziesenheim & Webb

[57] ABSTRACT

The invention relates to an analytical method for determining the organic halogen content of a sample. The results of the present method are superior to known methods, and are independent of the physico-chemical properties of the halo-organic compounds in the sample. The method comprises subjecting a sample containing a halo-organic compound, preferably in solution in an aprotic solvent, to electrolysis, and determining the resulting halide ion concentration.

12 Claims, No Drawings

PROCESS FOR DETERMINING THE ORGANIC HALOGEN CONTENT OF ORGANIC SAMPLES

The invention relates to a process of determining the concentration of halogen in organic samples, for example in chemical wastes. The total of organic halogen is indicated by the expression of TOX, in which X represents a chlorine, bromine, or iodine atom.

Organic halogen compounds, and especially the chlorine and/or bromine containing compounds, are important constituents of chemical wastes. Handling, use and draining of these substances are subject to strict rules in view of the possible danger of these substances to man and environment. Consequently, a reliable analytical method is indispensable.

The analytical instruments now available for determining the concentration of halogen in organic samples use various methods to determine the concentration. However, because these methods are based on certain physico-chemical properties of the halo-organic compounds which a number of the halo-organic compounds do not possess, it is not certain that a particular method will allow the determination of the total concentration of the organic halogen.

Presently, three analytical methods are being used, often in combination. In the first method, volatile halo-organic compounds are removed from a solution by bubbling an inert gas, for example nitrogen, through the solution and feeding the gas containing the halo-organic compounds in an oven where they are converted to hydrogen halide. Subsequently, the halide can be analysed coulometrically. The amount so determined is designated as volatile organic halogen (VOX).

In the second method an extraction is used, for example with diisopropyl ether, diisobutyl ketone or methylisobutyl ketone. The halide concentration in the extract is also determined coulometrically after destruction and oxidation in an oven. This amount is designated as extractable organic halogen (EOX). In a third method, the sample is passed through a column of active carbon and the halogen content of the active carbon is then determined by controlled combustion (pyrolizing the halo-organic compounds adsorbed to the active carbon) in an oven. The resulting hydrogen halide is analyzed coulometrically, as in the preceding methods. This amount is designated as adsorbable organic halogen (AOX).

It will be clear that a number of halo-organic compounds, such as those compounds which are non-volatile, non-extractable or non-adsorbable, cannot be analyzed with these methods. Illustrative in this respect is the 1980 leaflet of the Dohrman, Envirotech "Total organic halide analyzer", in which the yields for the adsorption to active carbon are very clearly governed by the polarity of the halo-organic compound. Thus, in case of 1-chlorodecane a yield of 100%, for chloroethanol a yield of 20% and for chloroacetic acid a yield of 0% is found. In view of this, the following equation will hold generally: $TOX \neq VOX + EOX + AOX$. This discrepancy is larger when the sample contains higher amounts of substances which cannot be removed by said methods. This is the situation for substances which cannot be removed by prior art methods (stripping, extraction, adsorption) due to the fact that they are polar and/or ionogenic. Such compounds cannot be extracted by a solvent less polar than water, and cannot be adsorbed onto active carbon.

Examples of halogenic compounds which cannot be analyzed with these methods are the halophenols, the haloanilines, the halocarboxylic acids, the sulphonated haloaromates etc. As, in practical cases, the nature of the halo-organic compounds is often not known, a determination of VOX, EOX and AOX gives a result which has an unknown relation to TOX. Therefore, the concentration of organic halogen found by this method will be too low in many cases. Additionally, the concentration of organic halogen found by this method will be too high in certain cases. This is the case when an organic substance is present as a salt with halide ion as counter ion, and this substance, on extraction, passes into the organic solvent so that its analysis will include the halide ions. Examples of these substances are quaternary ammonium chlorides.

The present invention relates to a totally novel method for analysis of halo-organic compounds, the result of which is independent of the physico-chemical properties of the substances to be determined, such as volatility, solubility or partition coefficient and adsorption characteristics. In the novel process the halo-organic compound is broken down by using cathodic reduction, and the liberated halide ions are determined. The reaction is $\text{org-X} + 2e^- \rightarrow \text{org}^- + X^-$. The advantage of this method resides in the fact that no differentiation is made between the polarity of the substances to be determined.

Therefore, the invention relates to a process for determining the concentration of halogen bound to organic compounds in an organic sample, in which a sample is subjected to electrolysis, and the resulting halide ion concentration is determined. The following conditions should be fulfilled for a successful analysis:

a. During the cathodic treatment all of the organohalogen bonds should be broken so that halide ions will be formed. In order to meet this requirement the halo-organic compounds should be dissolved in a suitable solvent. Some of these solvents are: acetonitrile, dimethylformamide, dimethylsulfoxide, dimethylacetamide and other so-called aprotic solvents. It appears to be unnecessary to use these solvents in anhydrous condition. For example, dimethylformamide having a water content of as high as 10% may be used without affecting the analysis. In fact, the aprotic solvent can contain water in a concentration of 0.1 to 40% by weight, but preferably in a concentration lower than 30% by weight. A suitable carrier electrolyte should be present as well, such as tetrabutylammonium tetrafluoroborate or other salts stable to negative cathodic potentials. Moreover, the electrode at which the cathodic, halide ions producing reaction proceeds, should be such a material that possibly interfering side-reactions, such as evolution of hydrogen, will be excluded as far as possible, i.e. the cathode should have a high hydrogen overvoltage. Such electrode materials are, for example, mercury, tin, lead, zinc, amalgamated metals, graphite, glassy carbon, etc. An optimum potential as well as effective stirring of the solution so as to improve the transport of the halo-organic compounds to the cathode, are required for keeping the electrolysis time as short as possible. The optimum potential can be found by determining a polarogram with a solution having the same composition, and deriving therefrom the potential at which the current is diffusion-dependent. It is highly advantageous to use proton donors, such as phenol, hydroquinone and similar hydroxyaromates so as to facilitate the cathodic release of halide ions. The proton donor is added in a concentration of 1 to 20 g/l, preferably in a concentration of 2 to 10 g/l.

b. Halide ions present in the sample will not interfere if their concentration is not too high with respect to the concentration of organic halogen. Should this be the case, the excess halide ions can be removed from the solution, for example by addition of an equivalent amount of $Ag^+$-ions in a medium in which the solubility of AgCl is low.

The electrolytic release of the halide ions is carried out in an electrochemical cell in which, preferably, no diaphragm, membrane or other separation between anode and cathode compartment is present. Such an electrochemical cell will prevent the occurrence of losses of organic substances through the separation and any volume change resulting from electro-osmotic solvent transport. In order to prevent the halide formed at the cathode in an electrochemical cell without a diaphragm from converting to halogen ($Cl_2$, $Br_2$, $I_2$) at the anode, and thus avoid subsequent determination, a depolarizer, such as hydrazine or hydroxylamine is added to the contents of the cell, so that the anode potential cannot rise to a high positive value. In this manner, the undesirable halogen formation is counteracted effectively. The depolarizer is added in a concentration of 1 to 25 g/l, preferably in a concentration of 5 to 15 g/l.

The analysis period may be limited by improving the transport of substances within the electrochemical cell by effective stirring of the liquid. In case mercury is used in the form of a mercury layer on the bottom of the electrolysis cell as the electrode material, stirring is preferably effected with a magnetic stirrer floating on the surface of the mercury, which stirrer is rotated by a rotating magnet positioned under the cell. Under such conditions a conversion of 90% within 5 minutes is feasible.

The invention is illustrated by the following examples.

EXAMPLE I

A cylindrical electrochemical cell provided with an amount of bottom mercury as a cathode, as well as of a platinum gauze at about 2 cm above the surface of the mercury as an anode, with a magnetic stirring element on the mercury surface, and with a saturated calomel electrode, was filled with about 20 ml of a solution of a chloro-organic compound having a concentration of about 50 mg/l. in dimethylformamide containing about 15% of water and 0.1 molar tetrabutylammonium tetrafluoroborate. The anode and cathode compartment were separated by a cation-permeable membrane. The cathode potential was fixed to −2.8 Volts by means of a potentiostat. After 10 minutes the chloride concentration of a sample of this solution was measured by means of a potentiometric titration. The yields of four chloro-organic compounds determined as chloride ions are given in table A.

TABLE A

| Compound | Yield % |
| --- | --- |
| 4-chlorobenzaldehyde | 99 |
| 1-chlorobutane | 97 |
| monochlorocyclohexane | 98 |
| monochlorobenzene | 95 |

EXAMPLE II

In the cell described in example I an experiment was carried out with pentachlorophenol as the chloro-organic compound. This substance was dissolved in dimethylformamide to which a slight amount of hydroquinone had been added. The carrier electrolyte and its concentration were the same as in example I. The yield of chloride ions derived from the chloro-organic compound was 96%.

EXAMPLE III

In a cell similar to that of example I, but without a membrane and with a platinum gauze anode having the same area as the surface of the mercury and being oriented parallel to it, an electrolysis was carried out with a solution of pentachlorophenol in dimethylformamide with 0.2 molar tetrabutylammonium tetrafluoroborate as the electrolyte. The solution also contained hydrazine in a concentration of 8 g/l. and hydroquinone in a concentration of 5 g/l. solution. The yield of chloride ions derived from the pentachlorophenol was 86% after an electrolysis period of 10 minutes and a cathode potential of −2.8 V.

EXAMPLE IV

In a cell as described in example III two electrolyses were carried out with solutions of 1,2,3tribromopropane in a concentration of 50 mg/l. in acetonitrile. The carrier electrolyte was tetrabutylammonium tetrafluoroborate in a 0.2 molar concentration. The solutions also contained hydrazine in a concentration of 8 g/l. The cathode potential was fixed to −2.5 V. with respect to a saturated calomel electrode.

In one of the experiments the solvent, acetonitrile, contained 30% of water. In acetonitrile solutions three experiments were performed with electrolysis times of 1, 2 and 5 minutes. When the electrolysis were completed the solutions were evaporated to dryness and the residues were taken up in ethanol containing 0.2% of nitric acid, and then the bromide concentrations were determined by potentiometric titration. The yields are given in table B.

TABLE B

| Halo-organic compounds | Solvent | Electrolysis time (min) | Yield (%) |
| --- | --- | --- | --- |
| 1,2,3-tribromo propane | acetonitrile | 1 | 65 |
| | | 2 | 82 |
| | | 5 | 99 |
| 1,2,3-tribromo propane | acetonitrile/ water, 70/30 | 5 | 100 |

EXAMPLE V

In a cell as described in example III two electrolyses were carried out with solutions of 2-bromophenol in a concentration of 100 mg/l. in acetonitrile. The carrier electrolyte was tetrabutylammonium tetrafluoroborate in a 0.2 molar concentration. The solutions also contained hydrazine in 0.25 molar concentration. In one case hydroquinone was added as a proton donor in 0.01 molar concentration. The cathode potential was fixed to −2.5 V. The bromide yields were measured in the same way as in example IV.

TABLE C

| Halo-organic compound | Proton donor | Electrolysis time (min) | Yield (5) |
| --- | --- | --- | --- |
| 2-bromophenol | hydroquinone | 5 | 25 |
| | | 20 | 50 |
| | | 45 | 84 |
| 2-bromophenol | — | 5 | 0 |

TABLE C-continued

| Halo-organic compound | Proton donor | Electrolysis time (min) | Yield (5) |
|---|---|---|---|
| | | 30 | 6 |
| | | 120 | 7 |

EXAMPLE VI

In a cell as described in example II an electrolysis was carried out with a solution of 1,2-dichloroethane in a concentration of 180 mg/l. in dimethylformamide. The carrier electrolyte and its concentration were the same as in example V. The solution contained hydrazine in 0.25 molar concentration. The electrode potential was fixed to −2.8 V. with respect to a saturated calomel electrode. The chloride ion yield was 87% after an electrolysis period of 30 minutes.

I claim:

1. A process for determining the concentration of halogen bound to organic compounds in an organic sample, which comprises the following steps:
    (a) subjecting a solution of the organic sample, an aprotic solvent, an electrolyte stable to negative cathodic potentials, a depolarizer, and a proton donor, to electrolysis, using a cathode consisting of a material having a high hydrogen overvoltage, while stirring the solution to thereby convert halogen bound to organic compounds to halide ions, and
    (b) determining the concentration of halogen bound to organic compounds in the organic sample by determining the concentration of halide ions formed in the solution resulting from step (a).

2. The process of claim 1, in which the aprotic solvent is acetonitrile, dimethylformamide, dimethylsulfoxide or dimethylacetamide.

3. The process of claim 1, in which the electrolyte stable to negative cathodic potentials is tetrabutylammonium tetrafluoroborate.

4. The process of claim 1, in which the cathode material having a high hydrogen overvoltage is selected from the group consisting of mercury, zinc, lead, tin, an amalgamated metal, graphite, and glassy carbon.

5. The process of claim 1, in which the depolarizer is selected from the group consisting of hydrazine and hydroxylamine.

6. The process of claim 1, in which the concentration of the depolarizer in the solution is 1–25 g/l.

7. The process of claim 1, in which the concentration of the proton donor in the solution is 1–20 g/l.

8. The process of claim 1, in which the aprotic solvent contains water in a concentration of 0.1–40% by weight.

9. The process of claim 1, in which the proton donor is an aromatic hydroxy compound.

10. The process of claim 9, in which the aromatic hydroxy compound is selected from the group consisting of phenol and hydroquinone.

11. The process of claim 1, in which any halide ions present in the solution before the electrolysis are removed from the solution.

12. The process of claim 11, in which any halide ions present in the solution before the electrolysis are removed by addition of an equivalent amount of silver ions to the solution.

* * * * *

UNITED STATES PATENT AND TRADEMARK OFFICE
CERTIFICATE OF CORRECTION

PATENT NO.  : 4,778,570

DATED       : October 18, 1988

INVENTOR(S) : Pieter J. Van Duin

It is certified that error appears in the above-identified patent and that said Letters Patent is hereby corrected as shown below:

Column 3 Line 15 "substances" should read --substance--.

Column 4 Lines 24-25 "1,2,3tribromopropane" should read --1,2,3-tribromopropane--.

Signed and Sealed this

Tenth Day of October, 1989

Attest:

DONALD J. QUIGG

Attesting Officer

Commissioner of Patents and Trademarks